United States Patent

Johs et al.

[11] Patent Number: 5,805,285
[45] Date of Patent: Sep. 8, 1998

[54] MULTIPLE ORDER DISPERSIVE OPTICS SYSTEM AND METHOD OF USE

[75] Inventors: Blaine D. Johs; Ping He; Steven E. Green; Shakil A. Pittal; John A. Woollam, all of Lincoln, Nebr.

[73] Assignee: J.A. Woollam Co. Inc., Lincoln, Nebr.

[21] Appl. No.: 818,445

[22] Filed: Mar. 17, 1997

Related U.S. Application Data

[63] Continuation-in-part of Ser. No. 530,892, Sep. 20, 1995, Pat. No. 5,666,201, which is a continuation-in-part of Ser. No. 265,325, Jun. 24, 1994, Pat. No. 5,501,706, and a continuation-in-part of Ser. No. 339,834, Nov. 14, 1994, Pat. No. 5,504,582, which is a continuation-in-part of Ser. No. 947,430, Sep. 18, 1992, Pat. No. 5,373,359.

[51] Int. Cl.$^6$ ................................................. G01N 21/21
[52] U.S. Cl. ............................................. 356/369; 250/225
[58] Field of Search ............................... 356/364–369, 356/381–382; 250/225

[56] References Cited

U.S. PATENT DOCUMENTS

| | | | |
|---|---|---|---|
| Re. 34,783 | 11/1994 | Coates ........................ | 250/372 |
| 4,030,835 | 6/1977 | Firester et al. ............... | 356/111 |
| 4,158,506 | 6/1979 | Collet ......................... | 356/365 |
| 4,200,396 | 4/1980 | Kleinknecht et al. ....... | 356/384 |
| 4,236,823 | 12/1980 | Roach et al. ................. | 356/351 |
| 4,541,716 | 9/1985 | Crooks et al. ............... | 356/237 |
| 4,681,450 | 7/1987 | Azzam ........................ | 356/367 |
| 4,725,145 | 2/1988 | Azzam ........................ | 356/367 |
| 5,045,704 | 9/1991 | Coates ........................ | 250/372 |
| 5,081,348 | 1/1992 | Siddiqui ..................... | 250/225 |
| 5,102,222 | 4/1992 | Berger et al. ................ | 356/367 |
| 5,337,146 | 8/1994 | Azzam ........................ | 356/367 |
| 5,373,359 | 12/1994 | Woollam et al. ............ | 356/328 |
| 5,504,582 | 4/1996 | Johs et al. ................... | 356/369 |
| 5,521,706 | 5/1996 | Green et al. ................. | 356/369 |
| 5,666,201 | 9/1997 | Johs et al. ................... | 356/369 |

FOREIGN PATENT DOCUMENTS 2069691  2/1980  United Kingdom .

OTHER PUBLICATIONS

Division–of–Amplitude Photopolarimeter Based on Conical Diffraction From Metallic Grating, Azzam, Applied Optics, vol. 31, No. 19, Jul. 1997.
Optics, Hecht, 2nd Ed Addison–Wesley 1987 (Selected Page).

*Primary Examiner*—Hoa Q. Pham
*Attorney, Agent, or Firm*—James D. Welch

[57] ABSTRACT

Disclosed is a dispersive optics system, in the context of sample substrate system investigating spectroscopic reflectometer and the like systems, which, in use, produce a plurality of "Orders" of essentially single wavelength beams of light from a polychromatic beam of light. In use the availability of more than one "Order" of essentially single wavelength beams of light allows simultaneous measurement of more essentially single wavelength beams of light, over a larger range, than would be possible were only one "Order" of essentially single wavelength beams of light present. Filters are present to reduce the effects of stray light on detector elements and to allow separating the wavelengths in overlapping regions of adjacent Orders. Also disclosed is a quadrant detector means of dispersive optics alignment, and a compensator means for reducing the effect of detector element polarization state dependence.

17 Claims, 4 Drawing Sheets

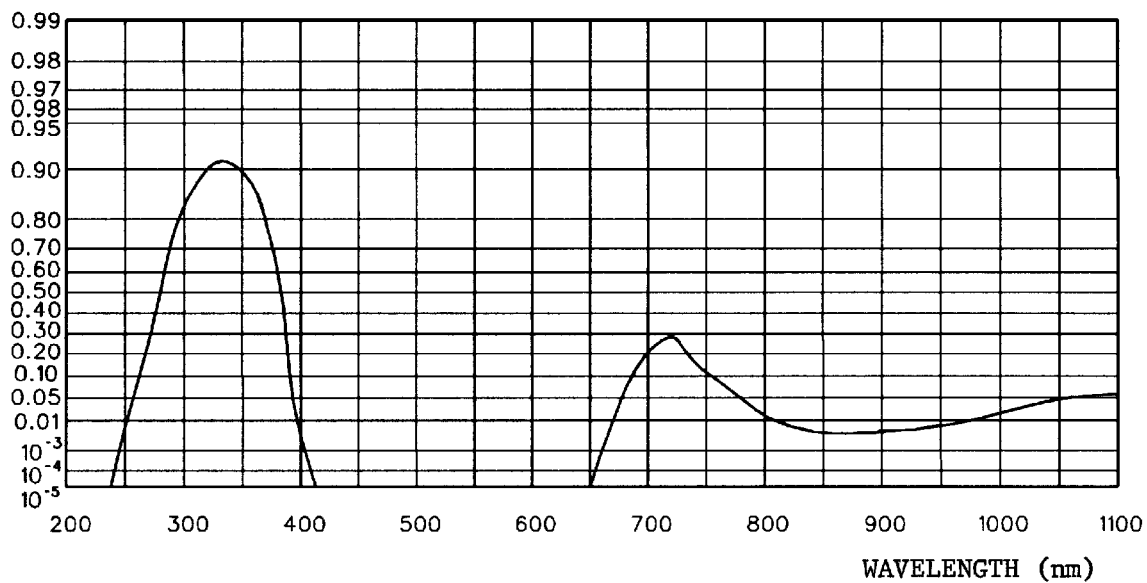
FIG. 8
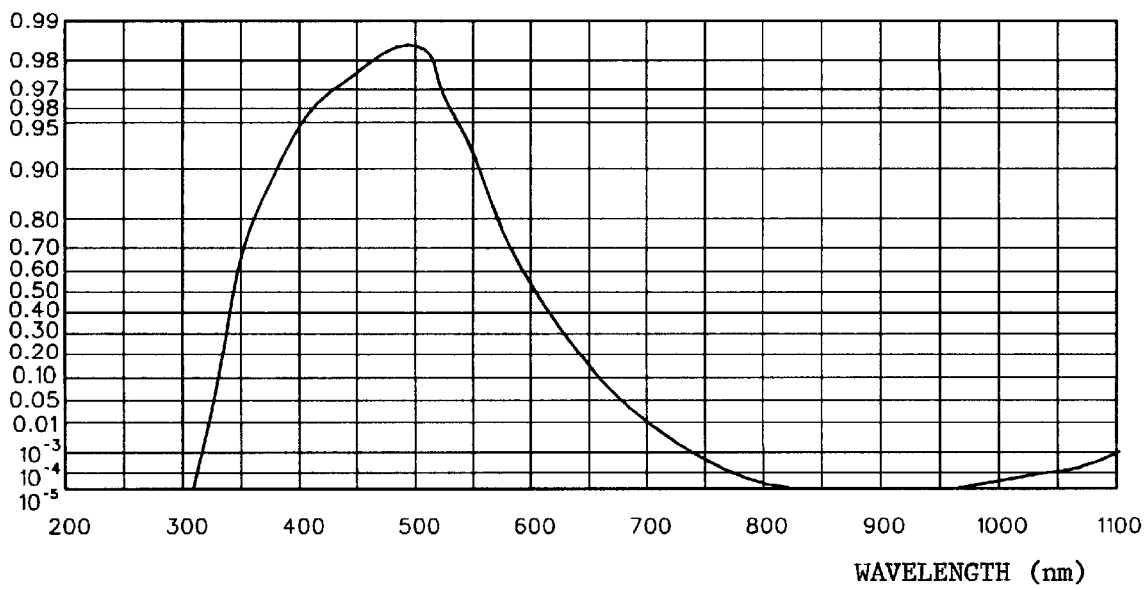
FIG. 9
FIG. 10

MULTIPLE ORDER DISPERSIVE OPTICS SYSTEM AND METHOD OF USE

This Application is a Continuation-In-Part of patent application Ser. No. 08/530,892 filed Sep. 20, 1995, (now U.S. Pat. No. 5,666,201), which in turn is a Continuation-In-Part of application Ser. Nos. 08/265,325 filed Jun. 26, 1994, and a continuation of 08/339,834 filed Nov. 14, 1994, (now U.S. Pat. Nos. 5,521,706 and 5,504,582 respectively), which in turn are Continuation-In-Part Applications of patent application Ser. No. 07/947,430 filed Sep. 18, 1992, now U.S. Pat. No. 5,373,359.

TECHNICAL FIELD

The present invention relates to reflectometer and the like systems, and more particularly to spectroscopic reflectometer and the like systems which enable simultaneous analysis of measured is signals derived from a multiplicity of essentially single wavelength beams of light, which essentially single wavelength beams of light are produced by interaction with a multiple "Order" producing dispersive optics system. The present invention system includes one or more filter(s), each comprised of one or more elements, to essentially eliminate the effects of stray light on detector elements, and to separate wavelengths present in overlapping portions of adjacent Orders. The present invention also includes a quadrature detector alignment system.

BACKGROUND

Reflectometer and the like systems, allow determination of Sample Substrate System physical and optical properties, (such as thickness, refractive index and extinction coefficient of surface films thereon), by detecting a change in wavelength presence and magnitude thereof in a beam of light which is caused to interact with said Sample Substrate System. References which provide insight to Reflectometry, and which are incorporated by reference hereinto, are "Optical Properties of Thin Solid Films", by O. S. Heavens, Dover Publications, New York, 1991; "Optical Processes in Semiconductors", by J. I. Pankove, Dover Publications, New York, 1971; and "Principals of Optics", by M. Born and E. Wolf, Perganon Press, Oxford, 1980. Patents which focus on determination of absolute Reflectance of a material in the ultraviolet range are U.S. Pat. No. 5,045,704 and RE 34,783 to Coates.

It is further noted for reference that Ellipsometer and Polarimeter systems measure a change in "Polarization State", which refers to a set of values for Polarized Light Beam Quadrature Components, (such as "S" and "P"), Magnitude Ratio, and a Phase Angle therebetween, (where "P" refers to that component which is in a plane containing the normal to a Sample System and incident and/or transmitted beam(s) of polarized light, and "S" refers to that component perpendicular thereto and parallel to the surface of said Sample System). It is also noted that a "full" polarization state also requires designation of an absolute value to which a magnitude ratio is referenced, and the direction of rotation of a polarized beam of light.

The present invention is applicable to essentially any Reflectometer, Ellipsometer or Polarizer and the like System and is focused upon the simultaneous production of a plurality of measurable Orders of essentially single wavelength polarized beams of light from a polychromatic beam of light, which polychromatic beam of light has been caused to interact with a Sample Substrate System. (Note that a Dispersive Optics System actually provides a continuous spectrum of spacially separated wavelengths which are present in a Polychromatic Beam Of Light. It is convenient, however, to view said spectrum as a multiplicity of essentially single wavelength beams of light. Such an approach has particular relevance where, because of size and placement, a Detector Element intercepts a relatively narrow band of said wavelengths centered about some central wavelength in a physically realized system).

A Patent, to Woollam et al. U.S. Pat. No. 5,373,359, presents a system of two Diffraction Gratings toward the end goal of the present invention, wherein a polarized beam of light Diffracted by one Diffraction Grating is caused to impinge upon another and provide a second spectrum of wavelengths. There exists, however, need for an improved approach to simultaneously providing a plurality of "Orders" per se. of polarized essentially single wavelength polarized beams of light. The reason for this is that simultaneous analysis of information in a plurality of essentially single wavelength polarized beams of light, which essentially single wavelength polarized beams of light are derived from a polychromatic polarized beam of light, which polarized polychromatic polarized beam of light has been caused to interact with a Sample System, allows more convenient characterization of more complex Sample Systems.

A U.S. Pat., No. 5,521,706 to Green et al., and a U.S. Pat. No. 5,504,582 to Johs et al., each describe the presence of a Dispersive Optics in a system which provides a detector array which intercepts a Single Order, in an spectroscopic rotating analyzer ellipsometer system.

A paper titled "Division-Of-Amplitude Photopolarimeter Based on Conical Diffraction For a Metallic Grating" by Azzam, in Applied Optics, Vol. 31, No. 19, 1 Jul. 1992 and U.S. Pat. No. 5,337,146 are also noted. The purpose of the System and Method of Use described in said references is to allow simultaneous measurement of all four Stokes Parameters of a Beam of Light. The System involved is a Crating which serves to provide Four Orders, each of which must be intercepted, possibly by a Detector Array. While the present invention System is to some extent similar to that alluded to in said Azzam references, it is to be appreciated that the Purpose to which the present invention System speaks, and the Method of Use thereof are very different than that described by Azzam. As well, the Azzam System, while providing for Polarization of wavelengths in certain Orders, does not provide for the filtering-out of stray light or of overlapping portions of adjacent Orders to provide wavelengths of an Order free of any masking influence of wavelengths present in an adjacent Order. The present invention provides that multiple element filters be present, which, in the context of Spectroscopic Reflectometer, (and Ellipsometer and Polarimeter) and the like systems has not, to the inventor's knowledge, not been previously known. (It is noted that application of the present invention to Ellipsometers and Polarimeters is covered in a pending patent application Ser. No. 08/530,892).

The present invention then, as taught supra in this Disclosure, is a multiple "Order" producing Dispersive Optics system and method of application thereof, for use in providing a multiplicity of essentially single wavelength polarized beams of light, in combination with Reflectometer, (and Ellipsometers and/or Polarimeters) and the like systems. The purpose thereof is to allow simultaneous detection and analysis of closely situated wavelengths, by interception thereof in different Multiple Order producing Dispersive Optics produced Orders, which closely situated wavelengths can not be simultaneously detected in a single Order because of Detector Element finite dimension limitations. As well, the present invention allows interception of different ranges of wavelengths in different orders, thereby allowing a compact system approach to extending the range of wavelengths which can be simultaneously detected.

DISCLOSURE OF THE INVENTION

The present invention is a Multiple "Order" Producing Dispersive Optics System in combination with a Spectroscopic Reflectometer and the like System, and Method of Application thereof.

As described in the Background Section, the ability to produce a polychromatic beam of light, cause it to interact with a Sample Substrate System, and then simultaneously analyze a multiplicity of essentially single wavelength beams of light derived therefrom present in a plurality of "Orders", in a Spectroscopic Reflectometer and the like system, enables convenient analysis and evaluation of defining parameters for complex Sample Substrate Systems, (eg. such as film thickness, refractive index and extinction coefficient or dielectric function real and imaginary components etc., of multiple layer thin films atop sample substrates). The present invention is focused upon the use of Multiple "Order" producing Dispersive Optics Systems in Spectroscopic Reflectometer and the like systems, to produce said multiplicity of essentially single wavelength beams of light in a plurality of "Orders", from a polychromatic beam of light which is caused to interact with a Sample Substrate System.

A primary example of the present invention Multiple "Order" Producing Dispersive Optics System is a Diffraction Grating, which Diffraction Grating Diffracts a polychromatic beam of light into a multiplicity of essentially single wavelength beams of light, when said polychromatic beam of light is caused to impinge thereupon at some predetermined angle. (Note, a Diffraction Grating is typically defined as a repetitive array of diffracting elements, either apertures or obstacles, which has the effect of producing periodic alterations in phase, amplitude, or both in an emergent wave, by the effect thereof on an incident wave. Alternating Opaque-Transparent Multiple-slit configurations can constitute "Transmission Amplitude Gratings", whereas essentially Fully Transparent Gratings with Parallel Lines etches therein can constitute Transmission Phase Gratings. Opaque Gratings with Lines etched therein similarly can be considered as Reflection Phase Gratings).

The Equation which describes the formation of a plurality of "Orders" by a Grating, from an incident polychromatic Beam of Light, each of which "Orders" contains a continuum of a multiplicity of essentially single wavelength beams of light is:

$$a*SIN(THETAm)=m*LAMBDA;$$

where "a" is the spacing of Grating Lines, "THETAm" is the angle at which a particular wavelength projects, "m" is the Order, (First, Second etc.), and "LAMBDA" is a wavelength.

If a polychromatic beam of light is incident upon a Diffraction Grating along other than a "Normal" thereto, the governing Equation is:

$$a*(SIN(THETAm)-SIN(THETAi))=m*LAMBDA;$$

where "THETAi" is the angle of incidence and the other symbols were defined above. Note that if "THETAm" equals "THETAi" the "Zeroth Order" results. While energy present in a "Zeroth Order" is not dispersed into a continuum of diffracted essentially single wavelengths, said "Zeroth Order" energy can at times be utilized, (for instance, where it reflects from the surface of a Diffraction (Grating in a direction other than coincident with the incident Beam of Light). It is noted that use of a "Blazed" "Reflection Phase Grating" can shift energy from a "Zeroth Order" and into higher more useful "Orders". Blazed Gratings have nonsymetrical Grating etchings, and involve a "Blaze Angle". This is described in "HECHT OPTICS, 2nd Edition, Addison-Wesley, 1987", which reference is incorporated herein by reference. Also, filters can be applied to the Zeroth-Order to provide specific wavelength(s) therein to a detector thereof.

To assure that the present invention is clearly disclosed, it is to be understood that, as used in this Disclosure, the term "Order" refers to a "Full Range" continuum of Diffracted Essentially Single Wavelength Beams of Light. When present, Multiple "Orders" are spacially separated from one another, but can "Overlap" one another. (Note that Filters are utilized to separate such "Overlapping Orders" and to essentially eliminate stray light entering a Detector Element). With this in mind it can be understood that a present invention Dispersive Optics System provides a plurality of "Full Range" "Orders" of essentially single wavelength beams of light, each of which spacially separated "Orders" of essentially single wavelength beams of light contains a "Full Range" continuum of wavelengths between some lower and some upper wavelength limit, when a source polychromatic beam of light is caused to impinge thereupon. The -wavelength content of an "Order" being limited only by the wavelength of a Light Source which provides a beam of light to an "Order" producing Dispersion Optics System.

The utility of the presence of a number of such "Orders" of spacially separated essentially single wavelength beams of light is based in the fact that physical size limitations prevent a Photodetector Array from providing a Detector Element therein at an appropriate location at which to intercept every desired essentially single wavelength beam of light in a single Order. That is, in a single "Order", the detecting of one essentially single wavelength beam of light prevents detecting a closely situated, (in space), essentially single wavelength beam of light, because the presence of one Detector Element positioned to intercept one essentially single wavelength beam of light prevents the presence of another Detector Element being simultaneously situated so as to be able to detect said closely situated essentially single wavelength beam of light. However, a beam of light of said closely situated essentially single wavelength, being also present in another "Order", can be simultaneously accessed therein by a Detector Element which can be positioned so as to Detect it. That is, if an essentially single wavelength beam of light can not be accessed in one "Order" because of physical Detector Element obstruction in the space thereof, it very likely can be accessed in another spacially offset "Order". As well, different ranges of wavelengths can be intercepted by photo detector arrays in different orders. This allows a geometrically based approach to extending the overall range of wavelengths which can be simultaneously detected.

The present invention system is then a Multiple-Order Producing Dispersive Optics System in combination with a Spectroscopic Reflectometer and the like system. In addition, and importantly, filters are present to essentially eliminate the effects of stray light and the effect of wavelengths in one Order on an adjacent Order, in regions of overlap therebetween. The Method of Application of the present invention involves utilization of said Multiple "Orders" to allow positioning Detector Elements so as to access desired essentially single wavelength beams of light of closely situated Wavelengths, and allows simultaneous detection of wavelengths in a larger overall range.

The present invention system can be more definitely described as a multiple order producing dispersive optics system in combination with a spectroscopic reflectometer system, which multiple order producing dispersive optics system produces a plurality of orders when a polychromatic beam of light is caused to impinge upon said dispersive optics system. Said orders are essentially spacially offset from one another and each said produced order comprises an essentially continuous spectrum of spacially separated light beams of essentially single wavelengths. Many of said essentially single wavelengths are present in two or more produced orders. In use first and second multiplicities of essentially single wavelength beams of light from first and second produced orders are simultaneously intercepted by, respectively, first and second photo detector arrays. This enables the simultaneous accessing of a first multiplicity of essentially single wavelengths by said first photo detector array and a second multiplicity of essentially single wavelengths by said second photo detector array. Each of said first and second multiplicities of essentially single wavelengths which are intercepted by said first and second photo detector arrays, respectively, includes specific first and second essentially single wavelength beams of light. Said specific first and second essentially single wavelength beams of light are simultaneously intercepted by specific detector elements in said first and second photo detector arrays respectively, even where light beams of said specific first and second essentially single wavelengths are spacially situated to close to one another in a single produced order for separate photo detector array detector elements in a single photo detector array which intercepts said single order, to, simultaneously, access beams of light of both said specific first and second essentially single wavelengths, separately. A method of use of the present invention system involves causing a polychromatic beam of light produced in said spectroscopic reflectometer system to interact with a sample system, impinge upon said multiple order producing dispersive optics and produce at least two orders, each of said produced orders comprising an essentially continuous spectrum of spacially separated essentially single wavelengths in a range of wavelengths which is similar in at least two orders; followed by accessing desired first and second essentially single wavelength beams of light by detector elements in, respectively, said first and second produced order intercepting photo detector arrays.

The present invention multiple order producing dispersive optics system, can then comprise a diffraction grating and filters to allow passage of wavelengths in one produced order, and not wavelengths in an adjacent spacially overlapping produced order, to a photo detector array. Said filters can further serve to prevent stray light from accessing said detector elements.

The grating can be selected of a "lined", a "blazed", or a "holographic" geometry. Said lined geometry consisting essentially of symmetrical alternating lines with depressions therebetween, and said blazed geometry consisting of alternating ramp shaped lines with depressions therebetween, and said holographic geometry consisting of continuous cosine shaped lines and depressions.

The dispersive optics system can, alternatively, comprise a Prism.

The present invention multiple order producing dispersive optics system can further comprise a retarder between an investigated sample substrate system and said dispersive optics system. The purpose thereof is to cause polarization entered to said polychromatic light beam by interaction with said sample substrate system to be other than essentially linear when entering said dispersive optics and detector elements, so that the effects of polarization state sensitivity of said detector elements is reduced.

The present invention spectroscopic reflectometer and the like system can comprise a source of a polychromatic beam of light, and means for causing said polychromatic beam of light to interact with a sample substrate system and a quadrant detector alignment means. Said quadrant detector alignment means typically comprises an center aperture surrounded by at least four detectors, such that in use said polychromatic beam of light, after interacting with said sample substrate system is caused to pass through said quadrant detector center aperture impinge upon said dispersive optics system and reflect a zeroth order back to said quadrant detector alignment means. The orientation of said dispersive optics is adjustable such that in use said dispersive optics can be positioned so that signals produced by each of said at least four detectors of said quadrant detector alignment means, which signals result from the amount of zeroth order impinging thereupon, are caused to be essentially equal.

A method of providing access to closely situated essentially single wavelength beams of light which also reduces polarization-dependence sensitivity of dispersive optics in reflectometer and the like systems, can comprise the steps of:

a. providing a spectroscopic reflectometer system comprising:
    a. a light source;
    b. a quadrant detector
    c. a dispersive optics; and
    d. photodetector systems;

such that, during use, polychromatic light from said light source is caused to reflect from a sample substrate system, such that said reflected polychromatic beam of light is, without further focusing, caused to pass through a central aperture of said quadrant detector, said quadrant detector being comprised of said central aperture surrounded by at least four detectors, such that said reflected polychromatic beam of light is caused to interact with said dispersive optics and emerge therefrom as a plurality of orders, each of which orders comprises a multiplicity of essentially single wavelength beams of light, which are caused to enter detector elements of photodetector systems for analysis therein;

b. causing polychromatic light to emerge from said light source and reflect from said sample substrate system, proceed through said quadrant detector, without further focusing after reflecting from said sample substrate system, and interact with said dispersive optics such that a plurality of orders, each of which comprises a multiplicity of essentially single wavelength, beams of light are produced;

c. adjusting the orientation of said dispersive optics such that a reflected zeroth order beam of light therefrom is caused to impinge on each of said at least four quadrant detector detectors in essentially equal intensities;

d. accessing desired essentially single wavelength beams of light in various of said orders by detector elements in photo detector arrays, which essentially single wavelength beams of light would otherwise be inaccessible as a result of physical constraints in a single order.

The present invention will be better understood by reference to the Detailed Description Section in this Disclosure, in conjunction with the accompanying Drawings.

SUMMARY OF THE INVENTION

It is therefore a purpose of the present invention to provide a multiple order producing dispersive optics system for application in reflectometer and the like systems.

It is another purpose of the present invention to teach that the present invention can be practiced in conjunction with essentially any reflectometer and the like system.

It is yet another purpose of the present invention to teach that, in use, closely situated essentially single wavelength beams of light can be detected in various orders, thereby allowing simultaneous detection thereof, where physical constraints would prevent such were but a single order available.

It is another purpose yet of the present invention to teach that, in use, a larger overall range of wavelengths can be simultaneously detected by interception of different ranges of wavelengths in different orders.

It is an additional purpose of the present invention to teach that, in use, filters should be applied to reduce stray light and separate the effects of adjacent orders in regions of overlap therebetween.

It another purpose yet, of the present invention, to teach that suitable dispersive optics systems for the practice thereof, include diffraction gratings, (reflective, transmissive, lined, Blazed, Hologram, Slited etc.), appropriate prisms and functional equivalents.

BRIEF DESCRIPTION OF THE DRAWINGS

FIG. 8 shows that a Filter (F1) can be comprised of Multiple Sections.

FIG. 9 demonstrates a filter (F1) section characteristic.

FIG. 10 demonstrates a filter (F1) section characteristic.

DETAILED DESCRIPTION

Figure 1A:
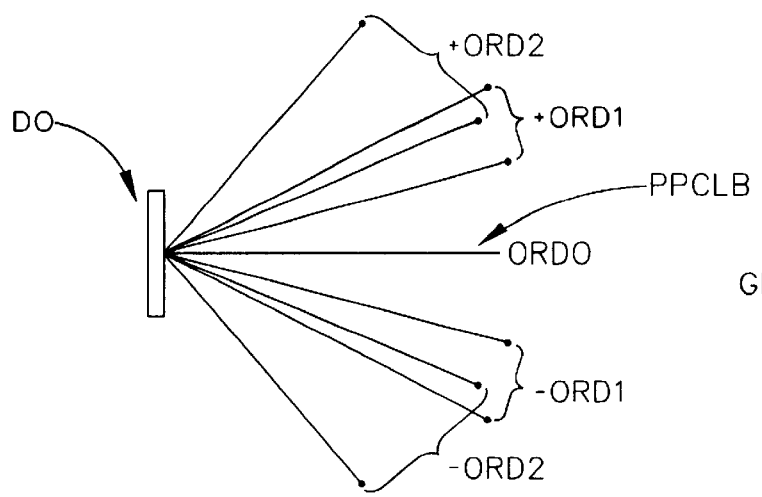
FIG. 1a shows a Dispersive Optics (DO) of the present invention accompanied by a plurality of "Orders" of polarized essentially single wavelength beams of light.

Turning now the Drawings, there is shown in FIG. 1a a Dispersive Optics (DO) upon which a Polychromatic Light Beam (PCLB), (shown superimposed on a zero Order (ORD0) reflection), is impinged, with the result being formation of a plurality of higher "Orders" (−ORD1, −ORD2, +ORD1 and +ORD2). Each higher "Order" being comprised of a continuum of wavelengths, conveniently viewed as a multiplicity of essentially single wavelength beams of light, each of which "Orders" has essentially equal lower and upper wavelength boundaries. The angular spacial separation spread, however, between contained essentially single wavelength beams of light in the higher Orders being typically larger than in lower Orders. Note that the higher Orders and lower Orders overlap, (ie +ORD1 and +ORD2 overlap and −ORD1 and −ORD2 overlap).

Figure 1B:
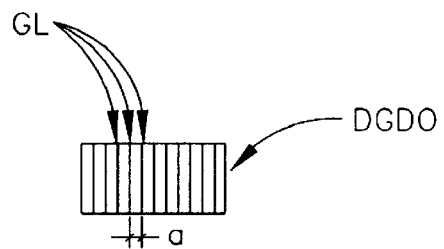
FIG. 1b demonstrates a Lined Grating.

FIG. 1b shows a "Gratting-Lined" (GL) Dispersive Optics Diffraction Gratting which could be applied to produce the "Orders" identified in FIG. 1a. In use a (PCLB) is caused to be incident upon the surface of the Diffraction Gratting Dispersive Optics (DGD0). Typically Grating Lines (GL's) are separated by a :distance "a", which is the "Groove Width". The spacial separation of wavelengths in an "Order" being described by the equation:

$$a*SIN(THETA)=N*LAMBDA,$$

where THETA is the angular spread of a Wavelength in an "Order" of number "N", (eq. 1 or 2), and LAMBDA is wavelength.

Figure 1C:
FIG. 1c demonstrates a Blazed Grating Line configuration.
Figure 1D:
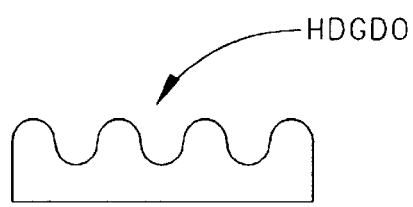
FIG. 1d demonstrates a Holographic Grating Line configuration.

FIG. 1c demonstrates a "Blazed" Diffraction Grating Dispersive Optics System (BDGDO), with "Blazed Grating Lines" Note the Blazed Angle (BA). Grating of this type, as opposed to those which provide simple symmetrically etched lines, can shift energy from a "Zeroth Order" into higher Orders. FIG. 1d shows a "Holographic" Diffraction Gratting Dispersive Optics System (HDGDO), in which the upper surface of present Diffraction Gratting Lines is of a repeating COSINE shape.

Figure 2:
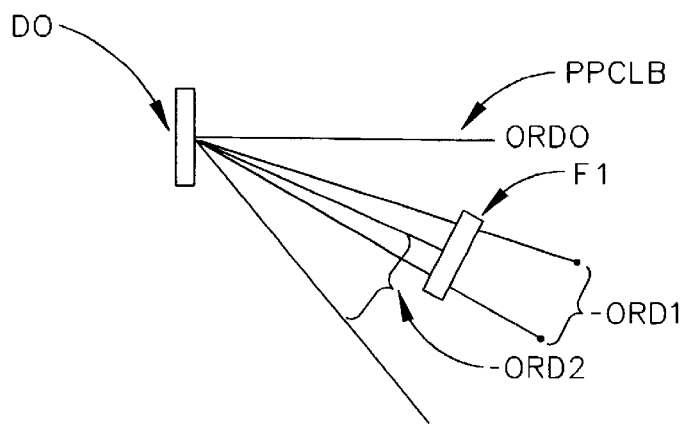
FIG. 2 shows the Dispersive Optics (DO) of the present invention accompanied by a two "Orders" of polarized essentially single wavelength beams of light.

FIG. 2 shows the Dispersive Optics (DO) of FIG. 1, with two of the overlapping "Orders", (−ORD1 and −ORD2), shown in FIG. 1 presented. Also shown is a Filter (F1) which serves to remove the higher Order (−ORD2) longer wavelength contribution leaving only shorter wavelengths from Order (−ORD1) present past said Filter (F1). While the intensity associated with a wavelength in a Second "Order" (ie. −ORD2 or +ORD2), is generally only approximately one-tenth (1/10) that associated with a First (−ORD1 or +ORD1), in the range of overlapping between "Orders", (eg. between −ORD1 and −ORD2 or between +ORD1 and +ORD2), the effect of a Second "Order" longer wavelength on the ability to measure a First "Order" shorter wavelength is not negligible, and typically must be filtered away to allow accurate First Order shorter wavelength Intensity measurements to be achieved.

Figure 3:
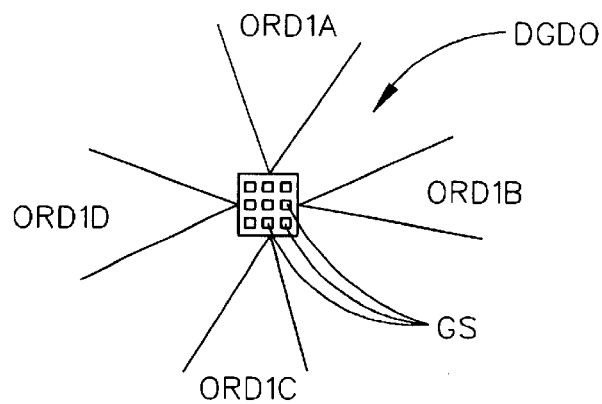
FIG. 3 shows a Grating which can provide four First Orders.

FIG. 3 shows that a Diffraction Gratting Dispersive Optics (DGDO) comprised of a Diffraction Gratting etched to have a multiplicity of "Grating Squares" (GS) thereon, and which can be utilized to provide four (4) First Orders (eg. ORD1A, ORD1B, ORD1C and ORD1D). It is noted however, that the energy which is present in the two First Orders (−ORD1 and +ORD1) of FIGS. 1 and 2, will be spread into four (4) First Orders as shown in FIG. 3. This means that the intensity in an Order where a greater number thereof are former, will be less than in a case wherein a fewer number of Orders are formed. Said intensity can be sufficient, however, to allow use of four such First Orders. Other Diffraction Gratting Geometries can provide other numbers of such First Orders.

Figure 4:
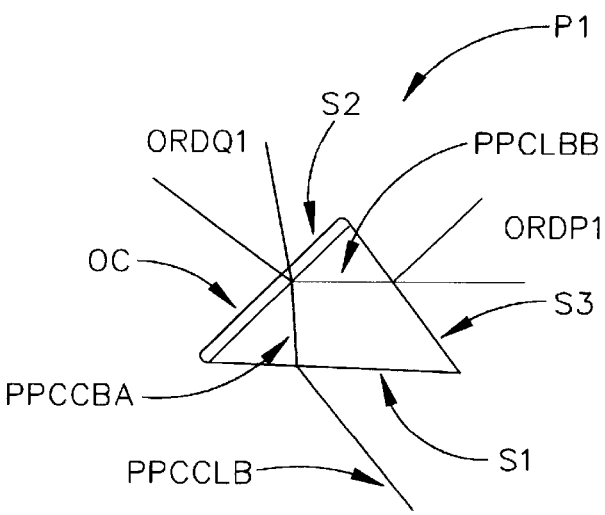
FIG. 4 shows use of a special Prism to provide two spacially spread continuums of essentially single wavelength polarized beams of light.

FIG. 4 shows a Prism (P1) which has three Surfaces (S1), (S2) and (S3). Surface (S2) is shown with a partially reflective coating (OC) thereon. A Polychromatic Light Beam (PPCCLB) is shown as incident on one surface (S1) thereof, and refracted to become (PPCCBA), which refracted beam is partially transmitted, and partially reflected, as (PPCLBB) at Surface (S2). Emerging from Surfaces (S2) and (S3) are Orders (ORDQ1) and (ORDP1). Said Orders contain essentially equivalent wavelength spectrums and spacial spread of wavelengths therein. The Intensities of wavelengths in the two Orders might be somewhat different depending on reflection/transmission efficiency and on longer additional pathway (PPCCBA+PPCLBB) and attenuation losses etc. of the (ORDP1) Order forming beam as compared to the (PPCCBA) pathway regarding the (ORDQ1) beam, however, both said Orders can be simultaneoulsy intercepted and utilized.

Figure 5:
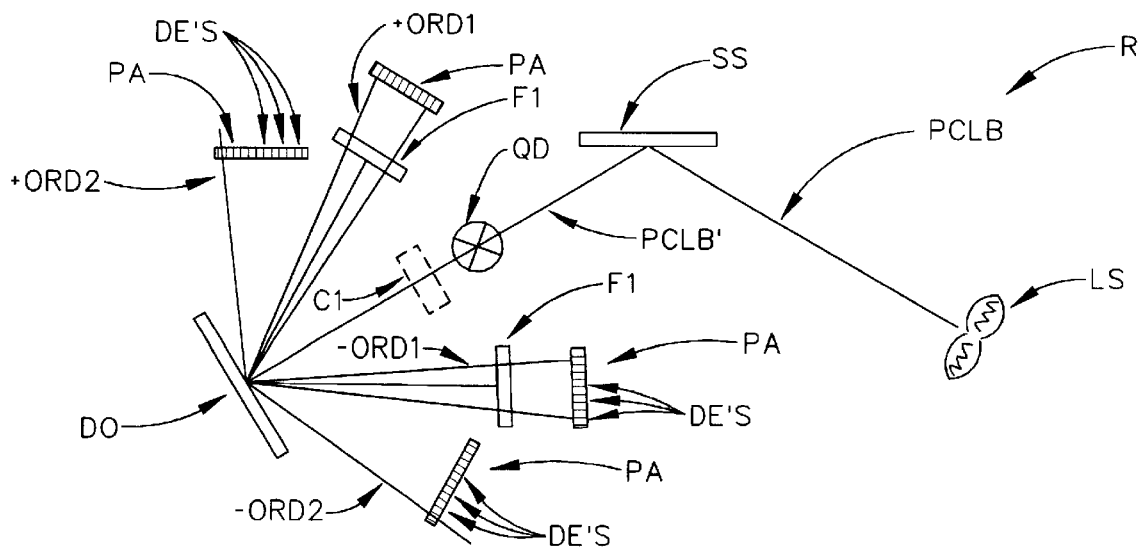
FIG. 5 shows the Dispersive Optics (DO) of the present invention accompanied by two "Orders" of polarized essentially single wavelength beams of light, in the context of a Reflectometer (R) System.

FIG. 5 shows a present invention Multiple Order producing Dispersive Optics (DO) in the context of a Spectroscopic Reflectomer (R) System. Said combination comprises a Light Source (LS), as well as Photodetector Arrays (PA's), each of which Photodetector Arrays (PA's) contains Detector Elements (DE's). In use said Light Source (LS) is caused to provide polychromatic light, which polychromatic light is caused to become a Polychromatic Light Beam (PCLB). Interaction with a Sample Substrate System (SS) serves to alter the Wavelength and Intensity content of said Polychromatic Light Beam (PCLB) in a manner which identifies physical and optical properties of said Sample Substrate System (SS). Said Polychromatic Light Beam (PCLB) is shown to, preferably without additional focusing thereof, interact with said Dispersive Optics (DO) and form a plurality of "Orders" (ie. −ORD2, −ORD1 and +ORD1, +ORD2), of Essentially Single Wavelength Polarized Beams of Light, each said "Order" being intercepted by Photodetector Arrays (PA's). Note that a Filter (F1) is present with respect to both Orders (−ORD1) and (+ORD1) to separate out the effects of (−ORD2) and (+ORD2) respectively, prior to said (−ORD1) and (+ORD1) being intercepted by said (PA's). It is also to be noted that the Photodetector Arrays (PA's) each contain a multiplicity of Detector Elements (DE's) which can be utilized to produce a signal which represents an essentially single wavelength beam of light.

Also note in FIG. 5, that the Photodetector Arrays (PA's) positioned to intercept essentially single wavelength light beams in the Second Order, (+ORD2) and (−ORD2), are shown oriented closer to the Dispersive Optice (DO), than Photodetector Arrays (PA's) associated with interception of essentially single wavelength beams of light in First Orders (+ORD1) and (−ORD1). This is to indicate that the angular spread between essentially single wavelength beams of light in Second Orders is generally greater than that in First Orders. Generally, one can adjust the distance from a Dispersive Optics (DO) at which a Photodetector Array (PA) is located in the present invention, so as to intercept a desired range of essentially single wavelength light beams.

FIG. 5 also shows, (in dashed lines), an optional Compensator/Retarder (C1) present between said Sample Substrate (SS) System and said Dispersive Optics (DO). Said Compensator (C1) can be present where the interaction of Polychromatic Light Beam (PCLB) with said Sample Substrate (SS) System effects a State of Polarization thereupon. It is to be understood that Detector Elements (DE's) can demonstrate Polarization State Sensitivity, and such is particularly pronounced where the Polychromatic Light Beam (PCLB') is Linearly Polarized. When utilized the Compensator (C1) serves to effect other than a Linear State of Polarization, preferably close to Circularly Polarized, upon said Polychromatic Light Beam (PCLB) prior to its entering said Detector Elements (DE's). (Note, Essentially circularly polarization refers to elliptical polarization in which magnitudes of "P" and "S" components of a polarized light beam are not exactly equal, and/or in which the phase angle therebetween is not exactly ninety (90) degrees, but in which said values are close to equal and/or ninety (90) degrees respectively). Said Compensator/Retarder might be variable, allowing a user to set the amount of retardance entered between "P" and "S" components of a polarized Beam of Light. The use of such a Compensator/Retarder is discussed in U.S. Pat. Nos. 5,521,706 to Green et al. and 5,504,582 to Johs et al. with respect to application of a retarder or depolarizing element in an Ellipsometer setting.

Figure 6A:
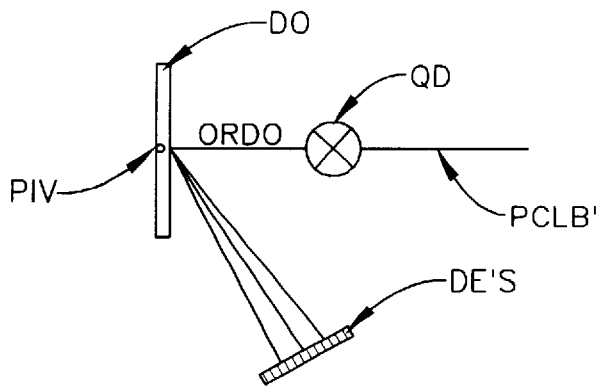
FIG. 6a shows the Dispersive Optics (DO) of the present invention accompanied by one "Order" of essentially single wavelength beams of light, in the context of a Reflectometer (R) System containing a Quadrant Detector (QD) alignment System.
Figure 6B:
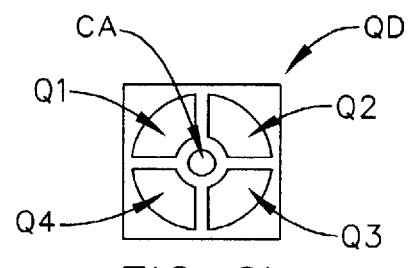
FIG. 6b shows the Quadrant Detector (QD) system of the present invention.
Figure 6C:
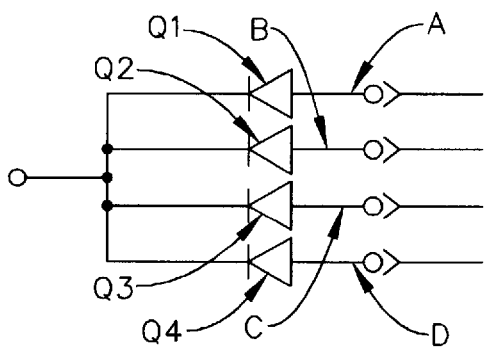
FIG. 6c shows the Quadrant Detector (QD) system of the present invention.
Figure 6D:
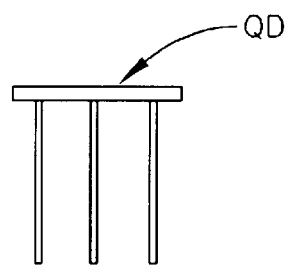
FIG. 6d shows the Quadrant Detector (QD) system of the present invention.

Turning now to FIGS. 6a–6d there is shown a partial view of the Quadrant Detector (QD) shown in the Spectroscopic Reflectometer (R) System of FIG. 5. In use the Polychromatic Light Beam (PLCB') which reflects from the Sample Substrate (SS) System passes through a Central Aperture (CA), (FIG. 6b shows the Central Aperature (CA) is surrounded by Detectors (Q1), (Q2), (Q3) and (Q4)), in said Quadrant Detector (QD), and interacts with the Dispersive Optics (DO), thereby providing First Order spacially separated essentially single wavelengths to the Detector Elements (DE's) in said Photodetector Arrays (PA's), whereat the presence and intensity of essentially single wavelengths are detected. It is to be understood that simultaneously, a Zeroth Order Polychromatic Light Beam (ORD0) will also be reflected back from the Dispersive Optics (DO), (as indicated in FIG. 6a), ideally essentially along the locus of the incident Polychromatic Light Beam (PCLB') to the Quadrant Detector (QD). In use, Alignment of the Dispersive Optics (DO) in the Spectroscopic Reflectometer (R) System is achieved by causing said Dispersive optics (DO) to rotate around a multi-axis Pivot (PIV) until all Quadrants of the Quadrant Detector (QD) monitor essentially the same signal strength. The Dispersive Optics (DO) Alignment procedure then comprises causing a beam of light to pass through a Central Aperature (CA) of a Quadrant Detector (QD) and impinge upon said Dispersive Optics (DO), with formation thereat of a Zeroth Order Light Beam which reflects back at said Quadrant Detector (QD). This is followed by adjustment of said Dispersive Optics (DO), such as about a Pivot (PIV) mounting, such that each Detector in the Quadrant Detector (QD) provide essentially the same intensity of output signal. Again, FIG. 6b shows that the Quadrant Detector has, typically, four separate Detectors (Q1), (Q2), (Q3) and (Q4) oriented about the Central Aperture (CA). It is also noted, however, that the Quadrant Detector (QD) is demonstrative and not limiting in that a Detector with other than four Detectors can also be utilized. FIGS. 6c and 6d show additional, practical, representations of said Quadrature Detector (QD).

FIG. 8 demonstrates that the Filter (F1) shown in FIGS. 2 and 5 can be of multiple Section, (a and b), construction, wherein each Section (a and b) has different filtering characteristics, as demonstrated by FIGS. 9 and 10 respectively. In use, the Filter (F1) Section "a", for instance, can serve to prevent stray light from entering a Detector Element, and "masking" passed ultraviolet wavelength light intensity. That is it allows only ultraviolet light to pass therethrough. Section "b", for instance, can serve to eliminate adjacent "Order" wavelengths from an "Order" of interest. That is, for instance, it passes wavelengths of four-hundred (400) to five-hundred (500) nanometers while blocking stray Ultraviolet and infrared wavelengths.

The present invention then simultaneously provides for use of a plurality of "Orders", each of which contains a continuum of essentially single wavelength beams of light, to allow simultaneous measurement of more essentially single wavelength beams of light than possible if only one "Order" were available. That is, wavelengths situated very closely to one another in a single order, can be simultaneously separately detected in separate orders, and different ranges of wavelengths can be detected in different orders, thereby allowing simultaneous detection of a broader range of wavelengths in two orders than is possible in a single order alone. Note that the present invention requires the presence of only one (1) Dispersive Optics (DO) to effect said result. While the production of a plurality of "Orders" is attended by a reduction in the amount of energy present in each, hence, in the Intensity associated with an essentially single wavelength beam therein, the benefits of having a plurality of wavelength spectrums to intercept and analyze include allowing simultaneous analysis of many more wavelengths than is possible if only one "Order" is available or utilized.

It is also noted that a specific embodiment of a Spectroscopic Ellipsometer System is taught in now U.S. Pat. No. 5,373,359 to Woollam et al., from which the present Application Continues. Said embodiment is applicable to the present Spectroscopic Reflectometer (R) System as well. That is the present invention Spectroscopic Reflectometer (R) System can comprise a Reflectometer for use in sensing characteristics of a sample substrate system comprising a light source and a dispersive optics system positioned so as to receive a beam of polychromatic light which reflects from said sample substrate system; wherein said dispersive optics system directs incident polychromatic light onto a photodetector array at a predetermined angle with respect to a normal to said dispersive optics system, with a precision of at least plus or minus one-half degree. Said precision being achieved by rotation of said dispersive optics (DO) system, (as shown in FIGS. 1a, 2, 5 and 6a in this present Disclosure), about an appropriate axis. It is specifically noted that the dispersive optics system in such a system, whether multiple Orders are produced thereby, and whether or not multiple Orders are utilized or not, can comprise Diffraction Gratings and/or Prisms and/or functional equivalents.

It is also to be understood that the terminology "Light Beam" has been used. This is to be taken to generally refer to electromagnetic radiation of any wavelength.

Figure 7:
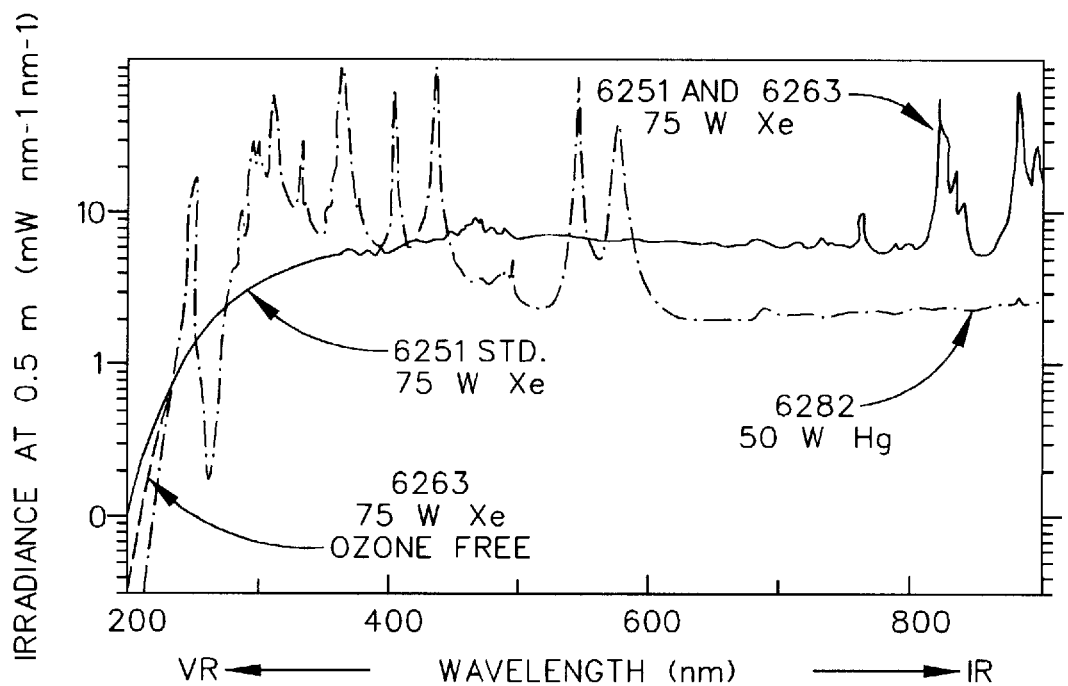
FIG. 7 shows the wavelength content of Xenon, and Mercury Vapor, Light Sources.

As well, it is to be understood that an "Order" will generally contain all wavelengths present in a beam of light incident upon an "Order" forming Dispersive Optics System. This can include from essentially zero to essentially infinitely long. However, if the source of said incident light is missing certain wavelengths, they, of course, are not to be expected to appear in a dispersed "Order". FIG. 7 shows plots of wavelengths present in, for instance, light provided by Mercury and Xenon lamps available from the "Oriel" Corporation. When said lamps are used as a Source of light, wavelengths present can be expected to be available in dispersed Orders, in relative intensities proportional to that provided by said Sources. A particularly suitable Light Source is a Xenon Lamp which provides polychromatic light with wavelengths in the range of from 0.25 to 1.7 microns. A quartz-tungsten halogen lamp can also be utilized if only wavelengths above approximately 0.4 micron are utilized.

It is to be understood that while an "Order" generally contains a continuum of wavelengths limited only by the content of a Light Source, it can be viewed as containing a spectrum comprising a multiplicity of essentially single wavelength beams of light. This approach is helpful when considering how a Photodetector Array (PA) intercepts an "Order", and was adopted herein. Finite dimension individual Detector elements (DE's) in a Photodetector Array (PA) are physically positioned to intercept a small band of wavelengths centered at an essentially single wavelength, which small band of wavelengths centered at an essentially single wavelength comprise an essentially single wavelength beam of light.

It is also disclosed that suitable Photodetector Arrays are available from E.G and G. Judson, 221 Commerce Dr., Montgomeryville, Pa, 18936, under the Product Number PDA38. Said chip containing the Photodiodes is approximately 15.2 millimeters wide, 51 millimeters long, 3 millimeters deep. The active area of the Photodiodes is approximately 3.8 square millimeters, with spacing between Detector Elements being a millimeter. It is noted however, that Photodetector Arrays with Detector Element spacing as small as thirty (30) microns are possible and within the scope of the present invention.

Suitable Detector Elements are also available from Electro-Optical Systems, Inc. at Greenway Technology Park, 1000Nutt Road, Pheonixville, PA, 19460.

It is noted that the Plots in FIGS. 9 and 10 are adapted from the materials of Schott Glass Technologies Inc.

A suitable Dispersive Optics System is a pivotally mounted Diffraction Grating which allows adjusting the angle at which a polychromatic beam of light: approaches thereto, with respect to a normal to a the surface thereof, is adjustable, preferably, to within plus or minus one-half (0.5) a degree. Said suitable Diffraction Grating also provides a spectrum of essentially single wavelength beams of light with wavelengths in the range of from 0.25 to 1.0+ microns.

Having hereby disclosed the subject matter of the present invention, it should be obvious that many modifications, substitutions, and variations of the present invention are possible in light of the teachings. It is to be understood that the invention can be practiced other than as specifically described, and should be limited in breadth and scope only by the Claims.

We claim:

1. A multiple order producing dispersive optics system in combination with a spectroscopic reflectometer system, excluding spectrosopic ellipsometer and spectroscopic polarimeter systems, which multiple order producing dispersive optics system produces a plurality of orders, which orders are essentially spacially offset from one another, when a polychromatic beam of light is caused to impinge upon said dispersive optics system, each said produced order comprising an essentially continuous spectrum of spacially separated light beams of essentially single wavelengths, many of said essentially single wavelengths being present in two or more produced orders; such that in use first and second multiplicities of essentially single wavelength beams of light from first and second produced orders are simultaneously intercepted by, respectively, first and second photo detector arrays, thereby enabling the simultaneous accessing of a first multiplicity of essentially single wavelengths by said first photo detector array and a second multiplicity of essentially single wavelengths by said second photo detector array, each of which first and second multiplicities of essentially single wavelengths intercepted by said first and second photo detector arrays, respectively, includes specific first and second essentially single wavelength beams of light, said specific first and second essentially single wavelength beams of light being simultaneously intercepted by specific detector elements in said first and second photo detector arrays respectively, even where light beams of said specific first and second essentially single wavelengths are spacially situated to close to one another in a single produced order for separate photo detector array detector elements in a single photo detector array which intercepts said single order, to, simultaneously, access beams of light of both said specific first and second essentially single wavelengths, separately.

2. A multiple order producing dispersive optics system as in claim 1, which comprises a diffraction grating, and in which filters are present to allow passage of wavelengths in one produced order, and not wavelengths in an adjacent spacially overlapping produced order, to a photo detector array, said filters further serving to prevent stray light from accessing said detector elements.

3. A multiple order producing dispersive optics system as in claim 2, in which said grating is selected from the group consisting of a "lined", a "blazed", and a "holographic" geometry, said lined geometry consisting essentially of symmetrical alternating lines with depressions therebetween, and said blazed geometry consisting of alternating ramp shaped lines with depressions therebetween, and said holographic geometry consisting of continuous cosine shaped lines and depressions.

4. A multiple order producing dispersive optics system as in claim 1, which comprises a Prism.

5. A multiple order producing dispersive optics system as in claim 1 in which the spectroscopic reflectometer system comprises a source of a polychromatic beam of light, means for causing said polychromatic beam of light to interact with a sample substrate system and a quadrant detector alignment means, said quadrant detector alignment means comprising an center aperture surrounded by at least four detectors, such that in use said polychromatic beam of light, after interacting with said sample substrate system is caused to pass through said quadrant detector center aperture impinge upon said dispersive optics system and reflect a zeroth order back to said quadrant detector alignment means; the orientation of said dispersive optics being adjustable such that in use said dispersive optics can be positioned so that signals produced by each of said at least four detectors of said quadrant detector alignment means, which signals result from the amount of zeroth order impinging thereupon, are caused to be essentially equal.

6. A multiple order producing dispersive optics system as in claim 5, which further comprises a retarder between an investigated sample substrate system and said dispersive optics system, other purpose thereof being to cause polarization entered to said polychromatic light beam by interaction with said sample substrate system to be other than essentially linear when entering said dispersive optics and detector elements, so that the effects of polarization state sensitivity of said detector element is reduced.

7. A method of providing simultaneous access to essentially single wavelength beams of light which, in a diffracted single order continuum of wavelengths are spacially situated to closely to one another for available photodetector elements to simultaneously detect, comprising the steps of:

a. providing a multiple order producing dispersive optics system in combination with a spectroscopic reflectometer system, excluding spectrosopic ellipsometer and spectroscopic polarimeter systems, which multiple order producing dispersive optics system produces a plurality of orders, which orders are essentially spacially offset from one another, when a polychromatic beam of light is caused to impinge upon said dispersive optics system, each said produced order comprising an essentially continuous spectrum of spacially separated light beams of essentially single wavelengths, many of said essentially single wavelengths being present in two or more produced orders; such that in use first and second multiplicities of essentially single wavelength beams of light from first and second produced orders are simultaneously intercepted by, respectively, first and second photo detector arrays, thereby enabling the simultaneous accessing of a first multiplicity of essentially single wavelengths by said first photo detector array and a second multiplicity of essentially single wavelengths by said second photo detector array, each of which first and second multiplicities of essentially single wavelengths intercepted by said first and second photo detector arrays, respectively, includes specific first and second essentially single wavelength beams of light, said specific first and second essentially single wavelength beams of light being simultaneously intercepted by specific detector elements in said first and second photo detector arrays respectively, even where light beams of said specific first and second essentially single wavelengths are spacially situated to close to one another in a single produced order for separate photo detector array detector elements in a single photo detector array which intercepts said single order, to, simultaneously, access beams of light of both said specific first and second essentially single wavelengths, separately;

b. causing a polychromatic beam of light produced in said spectroscopic reflectometer system to interact with a sample system, impinge upon said multiple order producing dispersive optics and produce at least two orders, each of said produced orders comprising an essentially continuous spectrum of spacially separated essentially single wavelengths in a range of wavelengths which is similarity at least two orders;

c. accessing desired first and second essentially single wavelength beams of light by detector elements in, respectively, said first and second produced order intercepting photo detector arrays.

8. A method of providing access to closely situated essentially single wavelength beams of light which also reduces polarization-dependence sensitivity of dispersive optics in reflectometer system, comprising the steps of:

a. providing a spectroscopic reflectometer system comprising:
        a. a light source;
        b. a quadrant detector
        c. a dispersive optics; and
        d. photodetector systems;

such that, during use, polychromatic light from said light source is caused to reflect from a sample substrate system, such that said reflected polychromatic beam of light is, without further focusing, caused to pass through a central aperture of said quadrant detector, said quadrant detector being comprised of said central aperture surrounded by at least four detectors, such that said reflected polychromatic beam of light is caused to interact with said dispersive optics and emerge therefrom as a plurality of orders, each of which orders comprises a multiplicity of essentially single wavelength beams of light, which are caused to enter detector elements of photodetector systems for analysis therein;

b. causing polychromatic light to emerge from said light source and reflect from said sample substrate system, proceed through said quadrant detector, without further focusing after reflecting from said sample substrate system, and interact with said dispersive optics such that a plurality of orders, each of which comprises a multiplicity of essentially single wavelength, beams of light are produced;

c. adjusting the orientation of said dispersive optics such that a reflected zeroth order beam of light therefrom is caused to impinge on each of said at least four quadrant detector detectors in essentially equal intensities;

d. accessing desired essentially single wavelength beams of light in various of said orders by detector elements in photo detector arrays, which essentially single wavelength beams of light would otherwise be inaccessible as a result of physical constraints in a single order.

9. A multiple order producing dispersive optics system in combination with a spectroscopic reflectometer system, excluding spectrosopic ellipsometer and spectroscopic polarimeter systems, which multiple order producing dispersive optics system produces a plurality of orders, which orders are essentially spacially offset from one another, when a polychromatic beam of light is caused to impinge upon said dispersive optics system, each said produced order comprising an essentially continuous spectrum of spacially separated light beams of essentially single wavelengths, many of said essentially single wavelengths being present in two or more produced orders; such that in use first and second multiplicities of essentially single wavelength beams of light from first and second produced orders are simultaneously intercepted by, respectively, first and second photo detector arrays, thereby enabling the simultaneous accessing of a first multiplicity of essentially single wavelengths by said first photo detector array and a second multiplicity of essentially single wavelengths by said second photo detector array, each of which first and second multiplicities of essentially single wavelengths intercepted by said first and second photo detector arrays, respectively, includes specific first and second essentially single wavelength beams of light, said specific first and second essentially single wavelength beams of light being simultaneously intercepted by specific detector elements in said first and second photo detector arrays respectively, even where light beams of said specific first and second essentially single wavelengths are spacially situated to close to one another in a single produced order for separate photo detector array detector elements in a single photo detector array which intercepts said single order, to, simultaneously, access beams of light of both said specific first and second essentially single wavelengths, separately; which multiple order producing dispersive optics system comprises one or more filter(s) which are utilized to separate wavelengths in regions in which adjacent orders produced thereby overlapping and to prevent stray light from having access to detector elements.

10. A multiple order producing dispersive optics system as in claim 9, in which at least one of the one or more filter(s) is of two section construction, with one section thereof being oriented in use so as to intercept wavelengths in a region of overlap between adjacent orders and allow wavelengths of essentially only one order to pass therethrough, and with another section thereof oriented so as to intercept and pass wavelengths of only one order, but reject stray light.

11. A multiple order producing dispersive optics system as in claim 10, in which one section of at least one filter passes only wavelengths in the ultraviolet.

12. A multiple order producing optics system as in claim 9, in which the spectroscopic reflectometer system, in addition to said one or more filter(s), comprises:

a. a light source;
b. a dispersive optics;
c. a compensator; and
f. photodetector systems;

such that, during use, polychromatic light from said light source is caused to reflect from a sample substrate system, thereby becoming at least partially polarized; such that said at least partially polarized polychromatic beam of light is, caused to pass through said compensator, such that said polarized light which exits said sample substrate system is, by passage through said compensator, caused to become other than linearly polarized, which other than linearly polarized beam of light which emerges from said compensator is then caused to interact with said dispersive optics and emerge therefrom as a plurality of orders, each of which comprises a multiplicity of essentially single wavelength beams of light, which enter detector elements of photodetector systems for analysis therein; such that in use polychromatic light is caused to emerge from said light source and reflect from said sample substrate system and after reflecting from said sample substrate system, interact with said dispersive optics such that a plurality of orders, each of which comprises a multiplicity of essentially single wavelength, other than linearly polarized, beams of light are produced and in which desired essentially single wavelength beams of light in various of said orders by detector elements in photo detector arrays are accessed, which essentially single wavelength beams of light would otherwise be inaccessible as a result of physical constraints in a single order.

13. A spectroscopic reflectometer system for use in sensing characteristics of a sample substrate system comprising:

a. a light source, and
b. a dispersive optics system positioned so as to receive a beam of polychromatic light which originates in said light source, and reflects from said sample substrate system; wherein said dispersive optics system directs incident polychromatic light onto at least one photodetector array at a predetermined angle with respect to a normal to said dispersive optics system, with a precision of at least plus or minus one-half degree.

14. A spectroscopic reflectometer for use in sensing characteristics of a sample substrate system as in claim 13, in which said dispersive optics system is a diffraction grating.

15. A spectroscopic reflectometer for use in sensing characteristics of a sample substrate system as in claim 14, in which said diffraction grating produces multiple orders in use.

16. A spectroscopic reflectometer for use in sensing characteristics of a sample substrate system as in claim 13, in which said dispersive optics system is a prism.

17. A spectroscopic reflectometer for use in sensing characteristics of a sample substrate system as in claim 15, in which said prism produces multiple orders in use.

* * * * *